United States Patent [19]

Toriyama et al.

[11] Patent Number: 4,988,362
[45] Date of Patent: Jan. 29, 1991

[54] COMPOSITION FOR COATING BIOCERAMICS, METHOD FOR COATING BIOCERAMICS THEREWITH, AND COMPOSITE BIOCERAMICS PRODUCED THEREWITH

[75] Inventors: Motohiro Toriyama, Kasugai; Sukezo Kawamura, Inuyama, both of Japan

[73] Assignee: Agency of Industrial Science & Technology, Ministry of International Trade & Industry, Tokyo, Japan

[21] Appl. No.: 319,757

[22] Filed: Mar. 7, 1989

[30] Foreign Application Priority Data

Mar. 30, 1988 [JP] Japan .................................. 63-77779

[51] Int. Cl.$^5$ .......................... A61F 2/28; A61K 1/02; C03C 10/02; C09K 3/00
[52] U.S. Cl. ..................................... 623/66; 623/16; 427/2; 427/201; 427/376.2; 427/397.7; 433/202.1; 433/212.1; 523/115; 106/35; 501/1; 501/10
[58] Field of Search ................. 623/16, 66; 433/201.1, 433/212.1; 106/35; 427/2, 201, 376.2, 397.7; 501/1, 10; 523/115, 116

[56] References Cited

U.S. PATENT DOCUMENTS 4,605,415  8/1986  Richez .................................. 623/16
4,681,633  7/1987  Watanabe et al. ..................... 106/35

Primary Examiner—Alan W. Cannon
Attorney, Agent, or Firm—Oblon, Spivak, McClelland, Maier & Neustadt

[57] ABSTRACT

A composition produced as a result of mixing alumina, silica, and a calcium phosphate compound in a specific ratio exhibits high affinity for bioceramics. When a bioceramic is coated with this composition and the coated bioceramic is heated, the composite is fused fast with the bioceramic to produce a composition bioceramic which is active to vital tissues.

6 Claims, No Drawings

ND COMPOSITE BIOCERAMICS
COMPOSITION FOR COATING BIOCERAMICS, METHOD FOR COATING BIOCERAMICS THEREWITH, AND COMPOSITE BIOCERAMICS PRODUCED THEREWITH

BACKGROUND OF THE INVENTION

1. Field of the Invention

This invention relates to a calcium phosphate type composition for coating bioceramics, a method for coating bioceramics, and composite bioceramics produced as a result of the coating. The composite bioceramics possess high strength and excel in bio-affinity and, therefore, prove to be useful as artificial bones, for example.

2. Prior Art Statement

Such ceramics as sapphire and sintered alumina possess high strength and manifest no toxicity in living organisms and efforts are being made to promote their use as bioceramics as artificial tooth roots, artificial bones and the like. These materials have a disadvantage in that since they are inert to vital tissues, they are incapable of binding themselves with neoplastic bones and are susceptible to "obvelation", i.e. of being enveloped in fibrous tissues by the living organism. Therefore, they cannot be kept implanted for a long time in a living body.

In contrast, such calcium phosphate compounds as hydroxyapatite and tricalcium phosphate are contained as main components of inorganic substances in living organisms and, therefore, possess outstanding bio-affinity manifesting safety to living organisms, ability to bind with bones, and ability to substitute for neoplastic bones. However, sintered articles of high-strength ceramics of calcium phosphate compound have never been produced.

In the circumstances, it is desirable to develop composite materials consisting of high strength ceramics such as sapphire and sintered alumina surfaces coated with a calcium compound for conferring bio-affinity.

As means of coating such bioceramics with the calcium phosphate compound, the flame spraying method, the sputtering method, the slurry method, etc. have been known to the art. The flame spraying method consists in fusing a powdered calcium phosphate compound in a flame of high temperature and spraying the resultant melt at a high speed on a substrate. Since this method requires use of an elevated temperature as described above, it has a disadvantage that the calcium phosphate compound yields to decomposition and induces alteration of the crystalline structure thereof. The sputtering method consists in sputtering the surface of a substrate with the calcium phosphate compound in a molten state. Since this method must be carried out under a high degree of vacuum, it inevitably suffers from poor productivity and high cost of production. The slurry method consists in spraying the substrate with a calcium phosphate compound in a slurry state, drying the applied layer of the slurry, and sintering the dried layer of slurry. This method has a disadvantage that the fastness of union between the substrate and the applied coating layer is not sufficient.

OBJECT AND SUMMARY OF THE INVENTION

This invention aims to provide an inexpensive and commercially feasible method for coating a substrate with a calcium phosphate compound, a composition used for the purpose of the coating, and a composite ceramic obtained by the method using the coating composition and to be used as a medical material excelling in bio-affinity.

The inventors continued a study with a view to accomplishing the object mentioned above and found that a coating composition prepared by mixing alumina, silica, and a calcium phosphate compound in a prescribed ratio, converting the composition in the form of slurry or film, coating the surface of a bioceramic with the slurry or film and subsequently subjecting the coated bioceramic to a heat treatment to adhere the coating composition on the bioceramic exhibits the desired qualities. The present invention has been completed based on this finding.

To be specific, this invention is directed to a coating composition for bioceramics consisting of a powder obtained by mixing alumina and silica in a gravimetric ratio in the range of 1 : 2 to 1 : 4 and a calcium phosphate compound incorporated in the powder in an amount in the range of 10 to 60% by weight based on the total weight of the powder, a method for coating a bioceramic characterized by coating the surface of the bioceramic with the coating composition mentioned above and thereafter subjecting the coated bioceramic to a heat treatment, and a composite bioceramic produced by the method mentioned above.

DETAILED DESCRIPTION OF THE PREFERRED EMBODIMENTS

For the preparation of the coating powder of the present invention, it is necessary first to mix alumina and silica in a gravimetric ratio in the range of 1 : 2 to 1 : 4, preferably 1 : 2.8 to 1 : 3.2. If the amount of alumina exceeds the upper limit of the range mentioned above, the produced composition is deficient in the fastness of adhesion to the bioceramic. Conversely, if this amount is less than the lower limit, the composition is inevitably deficient in the reactivity with the substrate. Then, the mixed powder consequently obtained is required to incorporate therein a calcium phosphate compound in an amount in the range of 10 to 60% by weight, preferably 20 to 50% by weight, based on the weight of the mixed powder. If the amount of the calcium phosphate compound exceeds the upper limit of the range mentioned above, the film to be formed of the composition is deficient in strength. Conversely, if this amount is less than the lower limit, the desirable quality of the calcium phosphate compound such as, for example, the ability to impart bio-affinity to the artificial bone, is not sufficient. The raw materials to be mixed herein in the form of powder are desired to possess an average particle diameter of not more than 1 micron.

The bioceramics which are usable for the present invention include alumina, sapphire, and zirconia, for example. These bioceramics are desirable as structural materials because they abound in strength and toughness and excel in safety. Further, these bioceramics notably gain in strength and toughness when they are locally given added density.

The calcium phosphate compound to be used advantageously in the present invention is hydroxyapatite or tricalcium phosphate, for example.

When the hydroxyapatite is employed as the calcium phosphate compound, it may be synthetic apatite which is produced by a dry method or a wet method. Otherwise, it may be bio-apatite reclaimed from the bones and teeth of various vertebrates.

Then, in the method of this invention, the coating composition obtained as described above (desirably in the form of powder) is converted into slurry or film and, in that state, is applied to coat the surface of a given bioceramic. The coated bioceramic consequently obtained must be given a heat treatment. This coating of the surface may be carried out, as generally practiced, by applying the slurry of the coating composition to the surface of the bioceramic, immersing the bioceramic in the slurry of the coating composition, or causing the film formed of the coating composition to adhere fast to the surface of the bioceramic. The slurry of the coating composition is desired to be an aqueous slurry suitable for application by spraying.

For the heat treatment to be given to the coated bioceramic, a method which consists in firing the coated bioceramic at a temperature in the range of 1,000° to 1,500° C., preferably 1,050° to 1,350° C. In this case, the heat treatment can be performed without requiring application of pressure. Optionally, it may be carried out under application of pressure as in the case of the hotpress method, for example.

In the course of the heat treatment in the method of this invention, the coating substance is thoroughly fused to the bioceramic. To be specific, the alumina, silica, and calcium phosphate compound in the coating composition form a liquid phase and come into sufficient contact with the bioceramic, a material given to be coated, during the initial stage of the heat treatment. Further, in the liquid phase, the alumina and the calcium phosphate compound react with each other to produce aluminum phosphate. The aluminum phosphate thus formed, by forming a solid solution with the unaltered calcium phosphate compound, enhances the fast union between the material being coated and the calcium phosphate compound and, during the course of cooling which follows the heat treatment, promotes the crystallization of the liquid phase formed of alumina, silica, and calcium phosphate compound, and augments the durability of the layer in the living organism.

In the bioceramics of the present invention, the coating generally has a thickness in the range of 0.01 to 10 mm, desirably 0.1 to 2.0 mm, and particularly desirably 0.2 to 1.0 mm. If the thickness of this coating exceeds the upper limit of the range mentioned above, the coating is deficient in strength. Conversely, if the thickness is smaller than the lower limit, the desirable quality of the calcium phosphate compound such as, for example, the bioaffinity required of the artificial bone is unduly inferior.

The composite bioceramics of the present invention can be used advantageously as artificial osseous materials such as, for example, artificial bones, artificial tooth roots, and artificial joints and can be implanted in the living body in much the same way as the conventional bioceramics.

The method of this invention, by thorough fusion, enables the calcium phosphate compound to be applied in the form of a coating to the surface of the bioceramics. Thus, the method manifests a conspicuous effect of being easily and inexpensively adaptable for commercial use.

The composite bioceramics obtained by the method of this invention possess high strength, excel in bioaffinity, and prove to be useful as for artificial osseous materials.

Particularly when the composite bioceramics are produced with a porous texture, they can be advantageously used as therapeutic materials in orthopedics, dentistry, and dental surgery because they can be easily substituted for neoplastic bones simply by being implanted in the living organism.

Now, the present invention will be described more specifically below with reference to working examples.

EXAMPLE 1

A coating composition was obtained by mixing alumina and silica in a gravimetric ratio of 1 : 3 and incorporating in the resultant mixed powder tricalcium phosphate powder in an amount of 20% based on the total amount of the mixed powder. Then, an aqueous slurry containing the composition in a concentration of 5% was applied by spraying to a sintered article of $\alpha$-alumina as a bioceramic. The coated bioceramic was dried and then heat-treated at 1,250° C. for one hour. As the result of this heat treatment, the surface of the sintered article of $\alpha$-alumina was coated with a layer of the calcium phosphate compound 0.3 mm in thickness. The calcium phosphate compound was found to be fused fast to the sintered article of $\alpha$-alumina.

EXAMPLE 2

A sintered article of $\alpha$-alumina coated with a layer of calcium phosphate type substance 0.8 mm in thickness was obtained by repeating the procedure of Example 1, except that the proportion of tricalcium phosphate in the coating composition was changed to 50% and the coating powder was deposited fast in the form of a compression molded film 1 mm in thickness on the sintered article of alumina.

COMPARATIVE EXPERIMENT 1

The procedure of Example 1 was repeated, except that the coating powder contained no tricalcium phosphate. In this case, the coating layer was not joined fast to the sintered article of alumina at all.

COMPARATIVE EXPERIMENT 2

The procedure of Example 1 was repeated, except that tricalcium phosphate powder was added to the coating powder in a proportion of 200% by weight. In this case, the coating layer was not joined fast to the sintered article of alumina at all.

What is claimed is:

1. A method for fusion of a bioceramic to the surface of a bioceramic inert to vital tissues, comprising:
   (A) coating the surface of said bioceramic inert to vital tissues with a bioceramic composition consisting essentially of a composition produced by mixing alumina and silica in a gravimetric ratio in the range of 1:2 to 1:4 thereby preparing a mixed powder and incorporating into said mixed powder a calcium phosphate compound in an amount in the range of 10 to 60% by weight, based on the amount of said mixed powder, thereby forming a coating layer on the surface of said bioceramic;
   (B) heating said bioceramic inert to vital tissues now provided with said coating layer thereby converting said coating layer into a solid solution containing aluminum phosphate formed by the reaction of calcium phosphate compound with alumina; and
   (C) cooling the resultant of (B), thereby accelerating crystallization of the coating layer.

2. A method according to claim 1, wherein said calcium phosphate compound is at least one member selected from the group consisting of hydroxyapatite and tricalcium phosphate.

3. A method according to claim 1, wherein said coating composition is apoplied in the form of slurry to the surface of said bioceramic.

4. A method according to claim 1, wherein said coating composition is applied in the form of a film formed mainly of said composition to the surface of said bioceramic.

5. A method according to claim 1, wherein said bioceramic is at least one member selected from the group consisting of alumina, sapphire, and zirconia.

6. A method according to claim 1, wherein said coated bioceramic is heated at a temperature in the range of 1,000° to 1,500° C.

* * * * *